United States Patent
Gupta et al.

(10) Patent No.: US 9,790,526 B2
(45) Date of Patent: Oct. 17, 2017

(54) CDNA ENCODING ENONE OXIDOREDUCTASE FROM MANGO

(71) Applicant: Council of Scientific and Industrial Research, New Delhi (IN)

(72) Inventors: Vidya Shrikant Gupta, Pune (IN); Ram Shridhar Kulkarni, Pune (IN); Ashok Prabhakar Giri, Pune (IN); Keshav H. Pujari, Dapoli (IN)

(73) Assignee: Council of Scientific and Industrial Research, New Delhi (IN)

( * ) Notice: Subject to any disclaimer, the term of this patent is extended or adjusted under 35 U.S.C. 154(b) by 225 days.

(21) Appl. No.: 14/376,404

(22) PCT Filed: Feb. 1, 2013

(86) PCT No.: PCT/IN2013/000072
§ 371 (c)(1),
(2) Date: Aug. 1, 2014

(87) PCT Pub. No.: WO2013/114407
PCT Pub. Date: Aug. 8, 2013

(65) Prior Publication Data
US 2016/0002685 A1    Jan. 7, 2016

(30) Foreign Application Priority Data
Feb. 3, 2012    (IN) .......................... 0304/DEL/2012

(51) Int. Cl.
*C12N 9/02*    (2006.01)
*C12P 17/04*    (2006.01)
*C12Q 1/68*    (2006.01)

(52) U.S. Cl.
CPC .............. *C12P 17/04* (2013.01); *C12N 9/001* (2013.01); *C12Q 1/6895* (2013.01); *C12Q 2600/13* (2013.01); *C12Y 103/01* (2013.01)

(58) Field of Classification Search
None
See application file for complete search history.

(56) References Cited

FOREIGN PATENT DOCUMENTS

WO    WO-2013/114407    8/2013

OTHER PUBLICATIONS

Ralph et al. BMC Genomics 2008; 9: 57.*
GenBank Accession No. EF148303; Mar. 24, 2009; [online] available at <http://www.ncbi.nlm.nih.gov/nuccore/ef148303>; Retrieved on Sep. 6, 2016.*
Lowe et al. Nucleic Acids Research 1990; 18: 1757-1761.*
Kulkarni et al. SpringerPlus 2013; 2: 494.*
"International Application No. PCT/IN2013/000072, International Search Report mailed Sep. 26, 2013", (Sep. 26, 2013), 4 pgs.

* cited by examiner

*Primary Examiner* — Angela M Bertagna
(74) *Attorney, Agent, or Firm* — Schwegman Lundberg & Woessner, P.A.

(57) ABSTRACT

Disclosed herein are primers for amplifying enone oxidoreductase, having a sequence selected from the group consisting of SEQ ID Nos. 1 to 13, from mango. Also disclosed herein is a nucleotide sequence of SEQ ID No. 14 encoding enone oxidoreductase, for enzyme production in an artificial system thus generating the desired flavor in food products.

5 Claims, 4 Drawing Sheets

Fig 1

```
ATGGAAACCATACTAGCATCAGCACCTTCTAAATTCACAAGCTTCCACTCATTTTCTCAGAG
GTTCTCCCTCGCCTTCGGGAAAATAGAAGGAAAAACGTTGTCAACGTTAACGGAGCGTCAT
CGTCTTACCTTCCTCTAATAGTTAGAGCAAATTCACAAGCTGCTCCTGCATCCACTGAGGCC
ACCAAGGTGAGTAGTGTACCCAGTGAAATGAAAGCGTGGGTGTATGGAGAATATGGAGGAGT
CGATGTATTGAAATTTGATGAGAAAGTTTCTGTGCCTCAAGTGAAGGAAGATCAGGTGTTGA
TCAAGGTTGTTGCTGCGGCTCTTAATCCTGTTGATGCTAAGCGAAGACAGGGCAAGTTCAAG
GCCACCGATTCTCCCTCCCGACTGTTCCAGGGTATGATGTAGCTGGTGTGGTGGTCAAGGT
TGGCAGTCAAGTGAAGGAATTTAAGGAGGGAGATGAGGTATATGGGACATAAATGAGAAGG
CACTGGAAGGGCCGAAACAATTTGGCTCCTTAGCCGAGTACACCGCAGTTGAAGAAAGTTA
TTGGCACTGAAACCAAAAAATTTGGATTTTGTTCAGGCTGCTGGCCTTCCTCTTGCTATTGA
GACGGCCTATGAGGGTCTAGAAAGAACTGGGTTCTCTGCTGGTAAATCTATTCTTGTTTTGA
ATGGTTCTGGTGGTGTTGGAAGCTTGGTGATTCAGCTAGCAAAACAAGTATTTGGTGCTTCA
AAAGTTGCCGCAACTTCAGGAACCAGAAACTTGGAACTTTTGAAGAGCTTGGGTACTGATTT
GGCTATTGACTACACCAAAGAAAATATTGAAGATTTGCCAGAAAAGTTTGATGTGGTCTATG
ATGCTATTGGGCAATGTGATCGAGCAGTAAAGGTAGTGAAAGAAGGGGGTGCTGTGGTGGCC
CTAACAGGTGCTGTAACACCTCCAGGCTTCAGATTTGTAGTTACTTCAAATGGAGCTGTTCT
GAAAAAATTAAATGCATTTCTAGAGAGTGGAAAGGTAAAGCCTGTAATAGACCCCAAGGGGC
CATTCCTTTCAGCCAGGTTATTGAGGCTTTCTCTTACATTGAAACGAACAGAGCTACTGGA
AAGGTGGTTATATACCCAATTCCTTAA
```

CDNA ENCODING ENONE OXIDOREDUCTASE FROM MANGO

PRIORITY CLAIM TO RELATED APPLICATIONS

This application is a U.S. national stage application filed under 35 U.S.C. §371 from International Application Serial No. PCT/IN2013/000072, which was filed Feb. 1, 2013, and published as WO 2013/114407 on Aug. 8, 2013, and which claims priority to India Application No. 0304/DEL/2012, filed Feb. 3, 2012, which applications and publication are incorporated by reference as if reproduced herein and made a part hereof in their entirety, and the benefit of priority of each of which is claimed herein.

FIELD OF THE INVENTION

The present invention relates to primer sequence for amplifying enone oxidoreductase derived from mango and an isolated nucleotide sequence encoding said Enone Oxidoreductase (EO) derived from *Mangifera indica*.

BACKGROUND OF THE INVENTION

Flavor is one of the most important attributes that decides the acceptability of various food items that we consume. The sensation of flavor perceived is generally because of the mixture of many chemicals in the food. Still, there are some compounds, which dominate the flavor of a particular food item and thus are themselves capable of eliciting a similar response in humans to that induced by food material. Furanones, which are found in many food products, represent one such dominating class of flavor compounds. Furanones are also important as naturally occurring flavor compounds. They are responsible for the caramel-like flavor of many fruits including strawberry, pineapple, raspberry, grapes, tomato, kiwi and mango. In addition to having a sweet and pleasant odour, furanones, especially furaneol and mesifuran, are characterized by a low odour detection threshold.

Earlier studies demonstrated that ripe mango fruits also contain high amounts of furaneol (4-hydroxy-2,5-dimethyl-3(2H)-furanone) and its methyl ether, mesifuran (2,5-dimethyl-4-methoxy-3(2H)-furanone). The fruits of cultivar Alphonso contained higher amounts of these compounds than any other cultivar and ripening of Alphonso fruits was characterized by de novo appearance and increase in the levels of these two furanones. Although furanones are not quantitatively the most dominant compounds of Alphonso fruits, the low odour detection threshold of furanones makes their contribution to Alphonso mango flavor, in terms of odour units, about 20-fold greater than that of any other volatile compound.

In spite of such crucial involvement of furanones in determining the flavor of mango and the other fruits, the biosynthesis of furaneol and mesifuran has until now been studied only in strawberry and tomato. Earlier studies on strawberry showed that out of several radiolabeled substrates fed to the ripening strawberry fruits, fructose-1,6-diphosphate had the highest rate of incorporation into furaneol. This, along with the other studies confirmed fructose-1,6-diphosphate as a natural precursor of furanones in the plants.

Further studies carried out to understand the biosynthesis of furaneol in plants indicate that fructose-1,6-diphosphate is first converted by an unknown enzyme into an unstable intermediate 4-hydroxy-5-methyl-2-methylene-3(2H)-furanone (HMMF). The furaneol forming enzyme, enone oxidoreductase which is highly similar to the NAD(P)H:quinineoxidoreductase, then reduces the exocyclic α, β unsaturated bond of HMMF, resulting in the formation of furaneol. Enone oxidoreductases from both, strawberry and tomato are capable of converting various derivatives of HMMF, substituted at the methylene group, into their respective saturated products. The presence of HMMF has also been detected in the fruits such as pineapple and raspberry suggesting that the biosynthetic pathway of furanones might be similar in different plants.

Furaneol further contributes to the fruit flavor by being converted into its methyl ether, mesifuran. The enzyme responsible for the formation of mesifuran is known only from strawberry and it was shown to be an S-adenosyl methionine dependent methyl transferase that methylates the hydroxyl group of furaneol.

An article titled "Functional characterization of enone oxidoreductases from strawberry and tomato fruit" by Klein D., published in J. Agric Food Chem. 2007 Aug. 8; 55(16): 6705-11 reports that HMMF, the substrate of FaEO that is formed during strawberry fruit ripening, was also detected in tomato and pineapple fruit by HPLC-ESI-MSn.

An article titled "Characterization of NAD(P)H-dependent Enone oxidoreductase of strawberry and tomato fruit" by Klein D., characterizes *Fragaria ananassa* enone oxidoreductase (FaEO) as an enzyme able to carry out two different reaction mechanisms depending on the available substrate. The enzyme from strawberry and a similar enzyme from tomato were heterologously expressed in *E. coli*, purified and biochemically characterized. The heterologously expressed enzyme catalyzed the formation of HDMF from D-fructose-1,6-biphosphate and NADH.

An article titled "Alternative oxidase from mango (*Mangifera indica*, L.) is differentially regulated during fruit ripening" by Cruz-Hernández A and Gómez-Lim M A published in Planta. 1995; 197(4):569-76, discloses analysis of alternative oxidase at the molecular level during the ripening of mango. Synthetic oligonucleotides, corresponding to conserved regions of the *Sauromatum guttatum* and *Arabidopsis thaliana* nucleotide sequences, were used as primers for polymerase chain reaction to amplify genomic DNA extracted from mango leaves. The 623-bp fragment was found to encode an open reading frame of 207 amino acids. Using this fragment one full-length cDNA clone, designated pAOMI.1, was obtained. The predicted amino-acid sequence exhibited 62, 64 and 68% identity to the *S. guttatum*, soybean, and *A. thaliana* enzymes respectively, indicating that this cDNA encodes a mango homologue of the alternative oxidase.

An article titled, "Ethylene biosynthesis and respiration during ripening in mango cultivars" by Reddy et. al. published in Indian Journal of Plant Physiology, 2001, Volume 6(4), 361-364, discloses the determination of enzymatic activities of ACC-oxidase and ACC-synthase at different stages of ripening in two varieties of mango fruits (*Mangifera indica* L.), viz. Amrapali and Dashehari. Among the two cultivars Dashehari showed higher level of ACC-synthase and ACC accumulation, and low level of ACC-oxidase, and ethylene production compared to Amrapali during the ripening process.

An article titled, "Expression profiling of various genes during the fruit development and ripening of mango' by Pandit et. al. published in Plant Physiology and Biochemistry, 48 (2010) explores several flavor related genes along with a few associated to the physiology of developing and ripening in 'Alphonso' mango. The temporal and spatial regulation of the genes during development and ripening of 'Alphonso' mango has been analyzed.

As seen from the above disclosures, nucleotide sequence encoding enone oxidoreductases (EO) which play an important role in the biosynthesis of furaneol in mango is not known hitherto and there is a long standing need in the prior art for such sequences. Hence the Inventors have attempted in this research to provide artificial sequences which may be used to impart color, flavor and smell as in natural Alphonso mangoes.

SUMMARY OF THE INVENTION

The main object of the present invention is to provide a primer sequence for amplifying enone oxidoreductase derived from mango.

Another object of the present invention is to provide a nucleotide sequence encoding enone oxidoreductase enzyme having an important role in the biosynthesis of furaneol in mango, for enzyme production in artificial system, for semi-biosynthesis of flavors.

Yet another object of the present invention is to provide a novel nucleotide sequence encoding enone oxidoreductase (EO) from mango, which is useful for enzyme production in an artificial system, for semi-biosynthesis of flavors, as well as and for improving various varieties of mango.

Accordingly, the present invention provides a primer sequence for amplifying enone oxidoreductase derived from mango selected from the sequence of Seq. ID No. 1-13.

In another aspect, the present invention provides the nucleotide sequence, Seq ID No. 14, encoding enone oxidoreductase enzyme having an important role in the biosynthesis of furaneol in mango for enzyme production in artificial system, for semi-biosynthesis of flavors.

In yet another embodiment of the present invention, use the sequences for semi-biosynthesis of flavors.

In still another embodiment of the present invention, use the sequences for enzyme production in artificial system.

In yet another embodiment of the present invention, use the sequences for improving mango varieties.

It is therefore an object of another aspect, to provide a novel nucleotide sequence encoding enone oxidoreductase (EO) from mango which is useful for enzyme production in an artificial system, for semi-biosynthesis of flavors, as well as for improving various varieties of mango.

Accordingly, in an aspect, the invention provides a novel nucleotide sequence encoding enone oxidoreductase derived from mango.

In another aspect, the present invention provides forward and reverse degenerate primers for enone oxidoreductase for the amplification of the cDNA prepared from ripe fruits of mango.

In yet another aspect, the present invention provides forward and reverse gene specific primers for enone oxidoreductase for the amplification of the ends of cDNA by rapid amplification of cDNA ends (RACE).

Yet another aspect, the current invention provides primers corresponding to the terminal regions of the mRNA which are designed for enone oxidoreductase. These terminal primers are used for the PCR amplification with mango cDNA as a template.

In yet another aspect, the invention provides a process of isolating gene sequence encoding functional enone oxidoreductase from mango.

In a further aspect, the invention provides process of biochemical characterization of the enone oxidoreductase isolated from mango.

DETAILED DESCRIPTION OF THE INVENTION

The invention will now be described in detail in connection with certain preferred and optional embodiments, so that various aspects thereof may be more fully understood and appreciated.

In order to provide a clear and consistent understanding of the specification, the following definitions are provided. Unless otherwise defined herein, all technical and scientific terms used here have the same meaning as commonly understood by one skilled in the art to which the invention belongs.

'Enone oxidoreductase' refers to an enzyme that catalyzes reduction of an enone compound.

MiEO in the specification refers to enyme Enone oxidoreductase derived from *Mangifera indica*

In an embodiment, the present invention discloses a novel nucleotide sequence encoding enone oxidoreductase isolated from mango. The nucleotide sequence encoding enone oxidoreductase is useful for enzyme production in an artificial system, plays an important role in the biosynthesis of furaneol in mango. Further, the artificially synthesized enzyme can be mixed appropriately with the food product, thus generating the desired flavor. The nucleotide sequence is also useful in the flavor industry for semi-biosynthesis of flavors via various approaches such as enzyme immobilization, single cell culture, etc., as well as for improving other varieties of mango.

Mature raw fruits of mango used in the present invention are collected from Dapoli, Deogad and Vengurle.

In an embodiment, the present invention provides a primer sequence for amplifying enone oxidoreductase derived from mango selected from sequence having Seq. ID Nos. 1-13.

Figure 1:
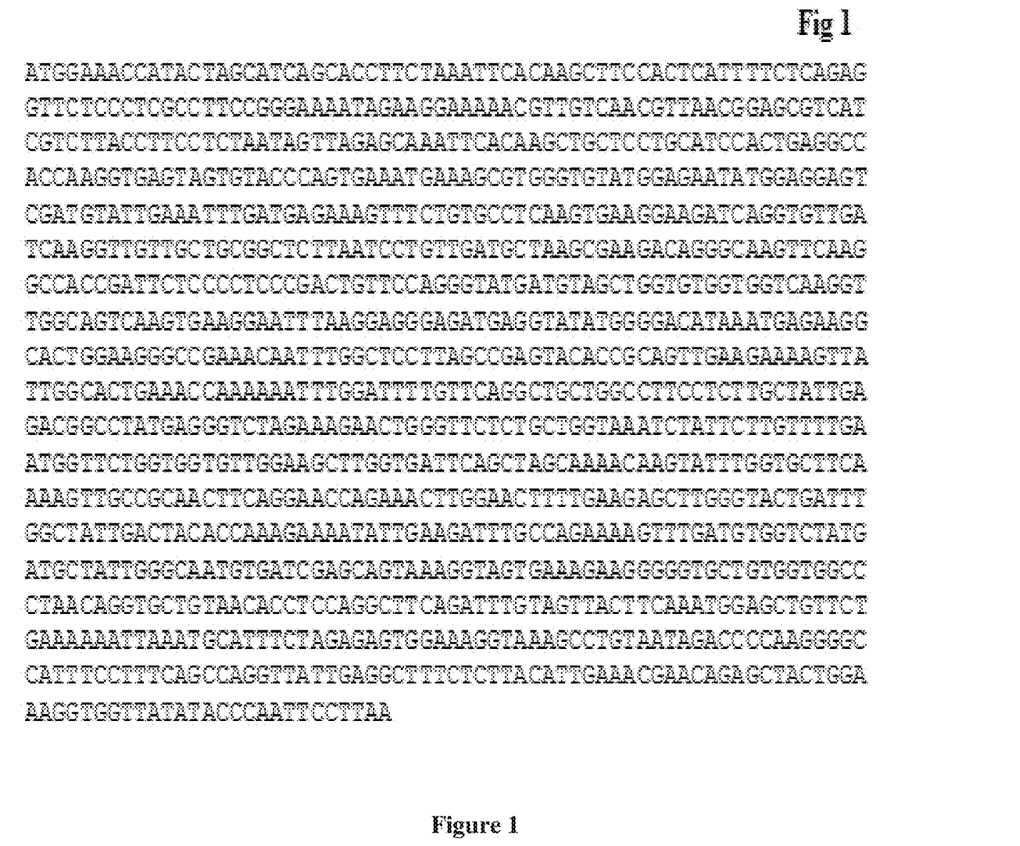
FIG. 1: Complete open reading frame encoding enone oxidoreductase isolated from mango (SEQ ID NO: 15).

In embodiment, the present invention discloses the complete open reading frame encoding enone oxidoreductase derived from mango as shown in FIG. 1.

Accordingly, the novel isolated nucleotide sequence encoding enone oxidoreductase comprises the sequence ID No. 14.

In an embodiment, the present invention provides forward and reverse degenerate primers for enone oxidoreductase for amplification of the cDNA prepared from ripe fruits of mango.

The degenerate primers (Seq. ID No. 1-7) designed for amplification of the mango cDNA are:

```
Forward1
                                    (Seq ID NO. 1)
GTKGTKGCTGCWKCYVTTAAYC Forward2
                                    (Seq ID NO. 2)
AARGMYAYYGAYTCTCCYYTRC Forward3
                                    (Seq ID NO. 3)
GGVWSWTTRGCWGARTAYACHGC Forward4
                                    (Seq ID NO. 4)
GTTYTRRRWGGHGCTGGKGGWGTTGG Reverse1
                                    (Seq ID NO. 5)
GRATSGGRTAYAYRACYACYTTYCC Reverse2
                                    (Seq ID NO. 6)
GCYYTHTCHSKYTSYCCWAYTGC Reverse3
                                    (Seq ID NO. 7)
RGTRGCTGCTAYYTTDGAWGCACC
```

In another embodiment, the present invention provides forward and reverse gene specific primers for enone oxidoreductase for amplification of the ends of cDNA by rapid amplification of cDNA ends (RACE).

The gene specific primers (Seq ID NO. 8-11) designed for amplification of the ends of mango cDNA are:

```
Forward1
                                    (Seq ID NO. 8)
CGAAGACAGGGCAAGTTCAAGGC Forward2
                                    (Seq ID NO. 9)
GGTGTTGGAAGCTTGGTGATTCAG Reverse1
                                    (Seq ID NO. 10)
GATTCTCCCCTCCCGACTGTTCC Reverse2
                                    (Seq ID NO. 11)
GGGTTCTCTGCTGGTAAATCTATTCT
```

In yet another embodiment, the current invention provides primers corresponding to the terminal regions of the mRNA which are designed for enone oxidoreductase. These terminal primers are used for the PCR amplification with mango cDNA as a template.

The terminal primers (Seq. ID NO. 12 and 13) designed for the PCR amplification are:

```
Forward
                                    (Seq ID NO. 12)
ATGAAAGCGTGGGTGTATGGAG Reverse
                                    (Seq ID NO. 13)
TTAAGGAATTGGGTATATAACCACC
```

The present invention further provides the process of isolating full-length nucleotide sequence (Seq ID no. 14) encoding enone oxidoreductase from ripe mangoes designated as MiEO. The process includes the following steps:

i. isolating RNA by CTAB method;

ii. treating total RNA with DNase and carrying out reverse transcription to obtain cDNA;

iii. designing degenerate primers for enone oxidoreductase based on the alignment of data base entries reported in the NCBI database;

iv. amplifying cDNA of step (ii) using the degenerate primers;

v. designing gene specific primers for enone oxidoreductase based on the sequence of the fragments obtained in step (iv);

vi. amplifying the ends of the cDNA using gene specific primers of step (v) by Rapid Amplification of cDNA Ends (RACE);

vii. designing primers corresponding to the terminal regions of mRNA based on the alignment of 5' and 3' RACE fragments with the enone oxidoreductase sequences reported from other plants; and viii. amplifying mango cDNA using primers designed in step (vii) by PCR (polymerase chain reaction) to obtain a full length cDNA of a putative mango enone oxidoreductase.

The process of isolating full-length sequence of enone oxidoreductase from ripe mangoes comprises isolation of RNA by CTAB method. After treating isolated RNA with DNase, reverse transcription is carried out. Based on the conserved regions in the nucleotide sequences of orthologous enone oxidoreductase (EO) reported in the NCBI database, designated as quinone oxidoreductases from *Fragaria×ananassa* (AY048861), *Vigna radiate* (U20808) and *Helianthus annuus* (AF384244), degenerate primers are designed. These primers are used for the amplification of cDNA prepared from ripe fruits of mango. This is followed by designing gene specific primers based on the sequence of the fragments obtained by amplification over the cDNA. The gene specific primers are used for amplification of the ends of the cDNA by rapid amplification of cDNA ends (RACE). Based on the alignments of the 5' and 3' RACE fragments with the respective sequences reported from the other plants, primers corresponding to the terminal regions of the mRNA are designed and are used for obtaining full-length sequence of MiEO.

The degenerate primers designed in step (iii) of the process of isolating full-length nucleotide sequence encoding enone oxidoreductase from ripe mangoes are as follows;

```
Forward1
                                      (SEQ ID NO: 1)
GTKGTKGCTGCWKCYVTTAAYC Forward2
                                      (SEQ ID NO: 2)
AARGMYAYYGAYTCTCCYYTRC Forward3
                                      (SEQ ID NO: 3)
GGVWSWTTRGCWGARTAYACHGC Forward4
                                      (SEQ ID NO: 4)
GTTYTRRRWGGHGCTGGKGGWGTTGG Reverse1
                                      (SEQ ID NO: 5)
GRATSGGRTAYAYRACYACYTTYCC Reverse2
                                      (SEQ ID NO: 6)
GCYYTHTCHSKYTSYCCWAYTGC Reverse3
                                      (SEQ ID NO: 7)
RGTRGCTGCTAYYTTDGAWGCACC
```

The gene specific primers designed in step (v) of the process of isolating full-length nucleotide sequence encoding enone oxidoreductase from ripe mangoes are as follows;

```
Forward1
                                      (SEQ ID NO: 8)
CGAAGACAGGGCAAGTTCAAGGC Reverse1
                                      (SEQ ID NO: 9)
GATTCTCCCCTCCCGACTGTTCC Forward2
                                      (SEQ ID NO: 10)
GGTGTTGGAAGCTTGGTGATTCAG Reverse2
                                      (SEQ ID NO: 11)
GGGTTCTCTGCTGGTAAATCTATTCT
```

The terminal primers designed in step (vii) of the process of isolating full-length nucleotide sequence encoding enone oxidoreductase from ripe mangoes are as follows;

```
Forward
                                      (SEQ ID NO: 12)
ATGAAAGCGTGGGTGTATGGAG Reverse
                                      (SEQ ID NO: 13)
TTAAGGAATTGGGTATATAACCACC
```

The complete open reading frame (ORF) of MiEO (Sequence ID No. 14) thus obtained is 1143 base pair long and is flanked by a 40 base pair UTR at the 5' end and by a 115 base pair UTR at the 3' end. The ORF encodes a protein having 381 amino acids, a calculated molecular weight of 40.6 kD and a pI of 8.61.

In another embodiment, the present invention studies the actual role of MiEO in forming the profiles of furanones observed during the ripening of mango fruit, where the transcripts of MiEO are profiled through various ripening stages. The highest expression of MiEO is detected at the 10 DAH (days after harvest) stage of the ripening fruits while a reduction in the expression of MiEO during the transition from 10 DAH to 15 DAH is observed.

Since ripe mango fruits contain high amounts of the furanones, furaneol and mesifuran, and since MiEO produces furaneol in in vitro assays, it is observed that the most likely in planta function of MiEO is the biosynthesis of furaneol.

Accordingly, in the ripening fruits of mango, the peak level of furanones is detected at the ripe stage (15 DAH); whereas, the highest expression of MiEO is seen at 10 DAH stage. This discrepancy can be attributed to the fact that peak transcript level and synthesis usually precedes the highest accumulation of a substance. However, in strawberry it has been shown that the expression of a similar gene, FaEO, is highly correlated with the furanone levels during fruit development. Several reasons can be given for the differences between strawberry and mango. Most importantly, strawberry is a non-climacteric fruit and mango a climacteric fruit and so there are notable differences in the ripening physiology of these two fruits and in the expression of various genes. Secondly, the level of furanones observed in mango is about 5 fold lower than in strawberry, while the precursor of furaneol, HMMF, is not detected in the mango fruits. The lack of a strong correlation between MiEO expression and furanone accumulation points towards involvement of MiEO in functions in addition to the biosynthesis of furaneol.

In another embodiment, the present invention studies the similarity of the in silico translated amino acid sequence of MiEO with enzymes from other plants. The similarity of the in silico translated amino acid sequence of MiEO is 79% with the chloroplastic alkenal/one oxidoreductase (AOR) from *Cucumissativus* (CsAOR), 73% with the enone oxidoreductase (EO) from *Solanumlycopersicon* (SlEO), 72% with the EO from *Fragariaxananassa* (FaEO) and 71% with the AOR from *Arabidopsis thaliana* (AtAOR). One such enzyme, CsAOR from *Cucumissativus*, which shows 79% sequence identity with MiEO, catalyses the reduction of α, β-unsaturated alkenals/alkenones in in vitro reactions. Similar oxidoreductase activity was also shown to be associated with an enzyme from *Arabidopsis* (AtAOR). The unsaturated aldehyde and ketone substrates of AORs, generated by lipid peroxidation, are highly reactive chemicals that can damage cellular activities by reacting with various biomolecules. Enzymes such as CsAOR and AtAOR are thought to be important for maintaining cellular processes by converting these harmful carbonyls into their saturated derivatives.

The analysis of the putative amino acid sequence of MiEO, strongly suggests that this protein might be localized in chloroplasts. This prediction can also be supported by the fact that chloroplasts are rich in fructose-1,6-diphosphate, the starting substrate for furaneol biosynthesis, which is produced by various pathways. Chloroplasts are also a center for production of highly reactive chemicals because of the high metabolic activity of this organelle, which can mainly be attributed to the process of photosynthesis and associated reactions. The increased rate of chemical reactions in chloroplasts of the fruits also results from the physiological transition of these organelles into chromoplasts, a most remarkable feature of fruit ripening. This conversion is characterized by various cellular changes such as dismantling of the thylakoid membrane system, which is brought about by degradation of its membrane lipids and chlorophylls, biosynthesis of carotenoids, and reduction in the amount of the proteins involved in photosynthesis. Some of these metabolic processes, especially the degradation of membrane lipids, are known to yield highly reactive compounds such as unsaturated carbonyls and reactive oxygen species. Since the chloroplast-located enzymes from the other plants, CsAOR and AtAOR, which are highly similar to MiEO have been shown to be involved in scavenging of the reactive compounds, it is possible that MiEO also might be involved in such processes instead of or in addition to the biosynthesis of furaneol. This hypothesis is supported by the fact that HMMF, the precursor of furaneol, is not detected in mango fruits. This observation along with the report of MiEO-like transcripts in the plants which have till now not been reported to contain furaneol (Table 1), and the absence of correlation between the transcript abundance of MiEO and the level of furanones in the mango fruits might be taken to support an alternative function of MiEO and a different biosynthetic pathway to the furanones.

TABLE 1

Uncharacterized sequences from the NCBI database showing high identity with MiEO

| Accession number | Plant | Putative annotation | Sequence identity with MiEO |
|---|---|---|---|
| XP_002525379 | *Ricinus communis* | Alcohol dehydrogenase | 94% |
| ABK96279 | *Populus trichocarpa* × *Populus deltoides* | Unknown | 90% |
| XP_002323668 | *Populus trichocarpa* | Unknown | 90% |
| ADN33837 | *Cucumis melo* | Alcohol dehydrogenase | 89% |

INDUSTRIAL ADVANTAGES

Furaneol and mesifuran are the two important ripening-related flavor chemicals of Alphonso mango. Biosynthesis of furaneol is catalyzed by enone oxidoreductase which has been isolated from the Alphonso mango fruits in this study. Mango is only the third plant after strawberry and tomato from which such gene has been isolated and characterized. This coding sequences can be used for biotechnological production of the recombinant enone oxidoreductase enzyme which can be used for the production of furaneol. The degenerate primers described here have been designed by homology-based approach based on the putative gene sequences reported from the other plants. These primers can thus be used for isolating similar genes from the other plants also. Similar work is being attempted by the Inventors in case of Alphonso mango as well as other economically important fruits and crops.

The novel nucleotide sequences of the present invention can be used for enzyme production in an artificial system and later this artificially synthesized enzyme can be mixed appropriately with any desired food product for generating the desired flavor. The nucleotide sequences can also be used for semi-biosynthesis of flavors via various approaches such as enzyme immobilization, single cell culture, etc., as well as to improve other varieties of mango. Also furaneol, the product of mango enone oxidoreductase, is an important flavor compound, which has huge application in the food industry.

REFERENCES CITED IN THE SPECIFICATION

Cruz-Hernández A, Gómez-Lim M A. (1995). Alternative oxidase from mango (*Mangifera indica*, L.) is differentially regulated during fruit ripening. Planta; 197(4):569-76.

Klein, D., Fink, B., Arold, B., Eisenreich, W. & Schwab, W. (2007). Functional characterization of enone oxidoreductases from strawberry and tomato fruit. *Journal of Agricultural and Food Chemistry* 55, 6705-6711.

Pandit, S. S., Kulkarni, R. S., Giri, A. P., Koellner, T. G., Degenhardt, J., Gershenzon, J. & Gupta, V. S. (2010). Expression profiling of various genes during the fruit development and ripening of mango. *Plant Physiology and Biochemistry (Paris)* 48, 426-433.

Reddy, Y. V., Srivastava, G. C., (2001) Ethylene biosynthesis and respiration during ripening in mango cultivars. *Indian Journal of Plant Physiology*. 6, 361-364.

EXAMPLES

The following examples are given by way of illustration and therefore should not be construed to limit the scope of the present invention.

Example 1

Plant Material

Mature raw fruits of mango were collected from the orchards of Konkan Krishi Vidyapeeth at Dapoli (N17°45' E73°11') and Deogad (N16°31' E73°20') and from a private orchard at Vengurle (N15° 51' E73° 39'). For each of the three localities, fruits were collected from four plants. After harvesting, fruits were put in the hay, carried to the laboratory and allowed to ripe at ambient temperature. At the interval of every five days, fruits were peeled, pulp was immediately frozen in the liquid nitrogen and stored at −80° C. until use. Thus, the experimental tissues of four ripening stages: 0, 5, 10 and 15 DAH (days after harvest) were obtained from each of the three localities.

RNA Isolation and cDNA Synthesis

RNA was isolated by CTAB method. After treating total RNA with DNase, reverse transcription was carried out over 1 µg of total RNA using Enhanced Avian RT First Strand Synthesis Kit (Sigma, St. Louis, Mo., USA).

Based on the conserved regions in the nucleotide sequences of orthologous enone oxidoreductase (EO) reported in the NCBI database, degenerate primers were designed. These primers were used for the amplification over the cDNA prepared from ripe mango fruits. The gene specific primers designed based on the sequence of the fragments obtained were used for amplification of the ends of the cDNA by rapid amplification of cDNA ends (RACE) using a RACE kit (Clontech, USA). Based on the alignments of the 5' and 3' RACE fragments with the respective sequences reported from the other plants, primers corresponding to the terminal regions of the mRNA were designed and were used for the obtaining full-length sequence of *Mangifera indica* enone oxidoreductase (MiEO).

The complete open reading frame (ORF) of MiEO thus obtained is 1143 base pair long (FIG. 1) and is flanked by a 40 base pair UTR at the 5' end and by a 115 base pair UTR at the 3' end. The ORF encodes a protein having 381 amino acids, a calculated molecular weight of 40.6 kD and a pI of 8.61.

Figure 2:
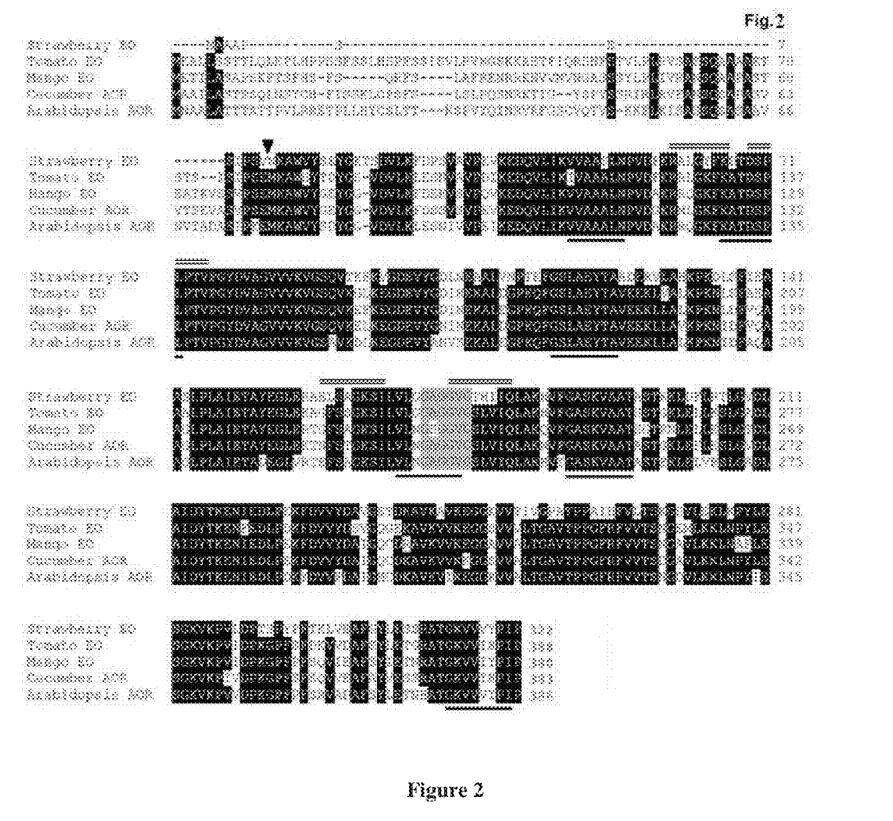
FIG. 2: Alignment of the in silico translated sequence of MiEO with the closest characterized sequences from other plants (SEQ ID NOS 18-22).

The in silico translated sequence of MiEO was alignment with the closest characterized sequences from other plants. The putative amino acid sequence of MiEO shows the presence of the conserved GxGxxG domain which is involved in binding with NADP. As shown in FIG. 2, regions of the alignment corresponding to the nucleotide sequence used for designing degenerate primers are marked by the line below the alignment, and that used for designing gene specific primers for RACE is indicated by double lines above the alignment. The conserved NAD(P)H-binding domain is highlighted in the grey color. The arrow head indicates the truncation site for removing the putative chloroplast targeting sequence.

Similar to CsAOR, AtAOR and SlEO, the N-terminal region of the in silico translated MiEO was characterized by the presence of putative chloroplast targeting peptide as revealed by analysis of the sequence by ChloroP program, suggesting that the MiEO protein might be localized in the chloroplast, as was shown for CsAOR.

Example 2

Expression Cloning and Recombinant Expression in *E. coli*

Full length sequence of MiEO was amplified using Expand High Fidelity PCR System (La Roche, Basel, Switzerland) with the terminal primers. cDNA prepared from the ripe fruit was used as the template and the resulting fragments of MiEO was cloned in the pCRT7-NT/TOPO expression vector (Invitrogen). Ligation reaction was transformed in the *E. coli* cells (Top10F', Invitrogen) and the transformants were selected on the LB-agar medium containing 100 µg/ml carbenicillin. The correct orientation of insert was confirmed by carrying out a PCR using forward T7 promoter primer and reverse gene specific primer, as well as by sequencing. The recombinant plasmids was transformed in BL21 (DE3) (Invitrogen) cells for recombinant expression. Starter culture (5 ml) grown for 48 hour at 18° C. in LB media was used as inoculum for the expression in 100 ml media with the Overnight Express Autoinduction System 1 (Novagen, USA). Cultures were grown for 24 hour at 18° C. and the pellet obtained after centrifugation was suspended in the buffer containing 25 mM MOPSO (pH 7.2) and 10% (v/v) glycerol. The cells were lysed by sonication and the $(his)_6$-tagged recombinant proteins were purified by passing the cleared lysate through Ni-NTA spin columns (Qiagen, Germany). Elution was carried out with the buffer containing 250 mM imidazole, 25 mM MOPSO (pH 7.2) and 10% (v/v) glycerol. Both crude lysate and the purified protein were checked for the presence and size determination of the recombinant protein by SDS-PAGE (Sambrook and Russell, 2001).

Example 3

Assay for the Enzymatic Activity

Purified protein was incubated overnight at 30° C. with 60 mg fructose-1,6-diphosphate and 3 mg NADH in 1 ml buffer containing 25 mM MOPSO and 10% glycerol (pH 7). The products formed were purified by solid phase extraction (SPE) using the DSC-18 columns having the capacity of 3 ml (Sigma, USA). The SPE column was first equilibrated with acetonitrile, followed by the assay buffer. After passing the incubation mixture, the products were eluted from the column with the help of dichloromethane and were analyzed by GC-MS. The product separation was carried out on the GsBP-5MS column having the dimensions of 30 m×0.32 mm i.d.×0.25 µm film thickness (General Separation Technologies, USA). Oven temperatures were programmed from 40° C. for 5 min, raised to 220° C. at 10° C. min-1 and held isothermal for 5 min. Injector and detector temperatures were 150 and 250° C., respectively. Helium was used as carrier gas at a flow rate 1 ml min-1. Mass spectra were obtained using Clarus 500 (Perkin Elmer) gas chromatograph-mass spectrometer at 70 eV with a scan time of 0.2 s.

To enhance the selectivity of the detection, only the ion of m/z 128 of furaneol was monitored. In the separate analysis total ion chromatograph was also recorded and was used for examining the spectra of the furaneol formed in the test assays.

Furaneol was detected in assays with the protein expressed from the plasmid having the reverse-oriented insert indicating that this activity is due to background proteins from the *E. coli* expression system. However, increasing the stringency of the wash solution to 40 mM imidazole during the purification of protein by affinity chromatography using Ni-NTA agarose spin columns resulted in diminishing of the oxidoreductase activity originating from *E. coli*.

Figure 3:
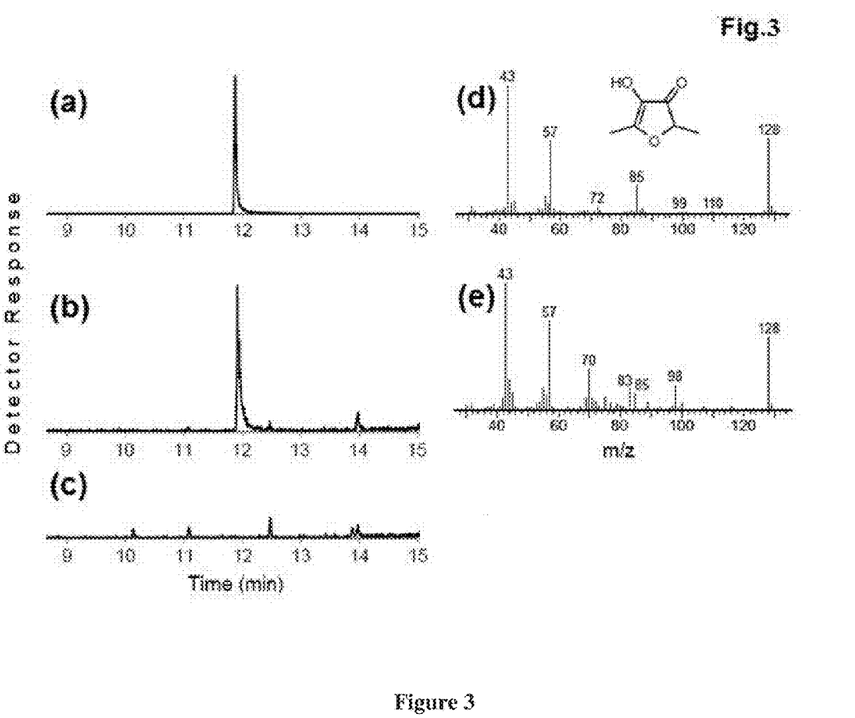
FIG. 3: GC-MS analysis of the products formed by MiEO. Depicted are traces (m/z 128) of samples of authentic furaneol (a), the products of reaction catalyzed by the protein expressed from MiEO (b) and the products of reaction catalyzed by protein extract from E. coli with the plasmid carrying the reverse-oriented insert (c) In a separate analysis, total ion spectra were obtained. The spectra represented are of the authentic furaneol (d) and of the furaneol detected in the assay with MiEO (e). The presence of m/z 70, 83 and 98 in (e) was because of the contaminating co-eluent; these ions were also detected at the same time in (c).

The MiEO protein purified and assayed with fructose-1, 6-diphosphate clearly showed the presence of furaneol as a reaction product in the GC-MS analysis (FIG. 3-*a, b, c, d, e*).

Although fructose-1,6-diphosphate is not a direct natural precursor of furaneol, the enzyme from strawberry, FaEO was also shown to be able to covert fructose-1,6-diphosphate to furaneol via an intermediate, HMMF. The detection of furaneol in assays of purified MiEO with fructose-1,6-diphosphate as substrate combined with the absence of furaneol in the assays of boiled protein thus confirmed the furaneol forming activity of MiEO.

Example 4

Quantitative PCR Analysis

Quantitative PCR was performed with Brilliant SYBR Green QPCR Master Mix (Stratagene, USA) with elongation factor 1α (EF1α) as a normalizing gene. Primers used for amplifying a fragment of MiEO were: (forward) 5'-AG-GTGCTGTAACACCTCCAGGCT-3' (SEQ ID NO: 16) and (reverse) 5'-CCTGGCTGAAAGGAAATGGCCCC-3'(SEQ ID NO: 17). Transcript abundance was quantified with a Mx3000P Real Time PCR Thermocycler (Stratagene) using a program with 45 cycles of 95° C. for 30 seconds, 63° C. for 30 secondsand 72° C. for 30 seconds, followed by a melting curve analysis of transcripts. The relative transcript abundance of the raw stage (0 DAH) of mango was considered and the fold difference for the rest of the tissues was calculated. Each measurement was repeated with four independent biological replicates, each of which was represented by at least two technical replicates. Ripening stages were compared to each other for the relative transcript abundance of each of the genes between the ripening stages and localities by ANOVA with the aid of Fisher's LSD at p≤0.05 using StatView software, version 5.0 (SAS Institute Inc., USA).

Figure 4:
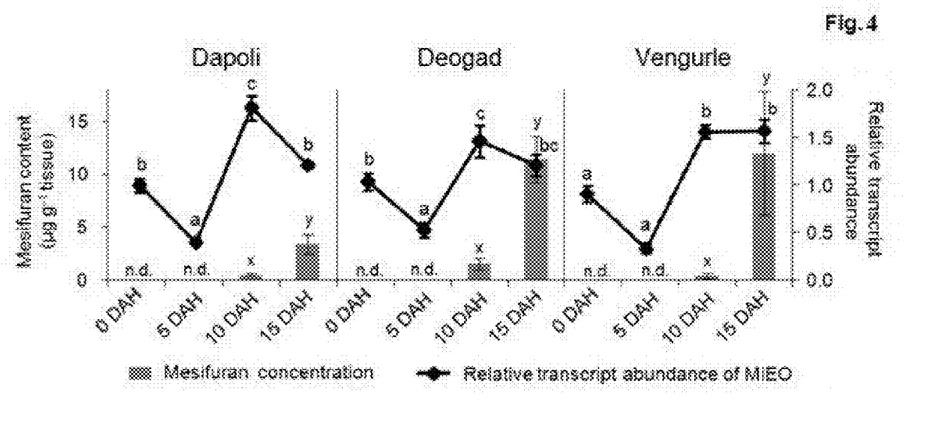
FIG. 4: Mesifuran content and relative abundance of MiEO transcripts in the ripening fruits of Alphonso mango from the three cultivation localities, Dapoli, Deogad and Vengurle in India (DAH: days after harvest. Letters indicate the significance of ANOVA ($p \leq 0.01$) for the comparison between the ripening stages for the levels of mesifuran (x, y, etc.) and the relative transcript abundance of MiEO (a, b, etc.); the values having different letters are significantly different from each other.

The highest expression of MiEO was detected at the 10 DAH (days after harvest) stage of the ripening fruits (FIG. 4). As can be seen in FIG. 4, the relative transcript abundance of MiEO for the raw stage (0 DAH) from Dapoli was considered 1 and the fold difference for the rest of the tissues was calculated. There was a reduction in the expression of MiEO during the transition from 10 DAH to 15 DAH (ripe) fruits. Although furaneol and mesifuran are completely absent in the raw fruits (0 DAH), the expression level of MiEO was only about 1.5-fold lower than in the ripe fruits. There was about two fold reduction in expression during the transition of fruit from 0 to 5 DAH stage. Out of the three localities which were studied for the content of volatiles, Dapoli was characterized by the lowest amount of mesifuran in the ripe fruits; whereas, for the 10 DAH stage, the highest amount of mesifuran was detected in the fruits from Deogad. To know if there is any contribution of MiEO to such geographic variation, expression of MiEO was also analyzed in the ripening fruits of mangoes from these cultivation locations. Although there were some differences between the localities for the level of MiEO transcripts, the pattern could not be correlated with the varied mesifuran content among the localities.

We claim:

1. A bacterial host cell comprising a vector comprising a promoter operably linked to a cDNA comprising SEQ ID NO: 14.

2. The bacterial host cell of claim 1, wherein the bacterial host cell is an *E. coli* cell.

3. A method for semi-biosynthesis of flavors, comprising:
expressing in vitro a cDNA comprising SEQ ID NO: 14 so as to yield an enone oxidoreductase;
isolating the enone oxidoreductase; and
contacting the isolated enone oxidoreductase with a substrate therefor under conditions for producing a mixture having a flavor as a result of conversion of the substrate to 4-hydroxy-2,5-dimethyl-3(2H)-furanone) by the enone oxidoreductase, wherein the conditions include the presence of a co-factor.

4. The method of claim 3, wherein the enone oxidoreductase is immobilized on a surface between the isolating and contacting steps.

5. A method for enzyme production, comprising: expressing in vitro the cDNA of claim 1 so as to yield an enone oxidoreductase.

* * * * *

```
                         SEQUENCE LISTING

<160> NUMBER OF SEQ ID NOS: 22

<210> SEQ ID NO 1
<211> LENGTH: 22
<212> TYPE: DNA
<213> ORGANISM: ARTIFICIAL SEQUENCE
<220> FEATURE:
<223> OTHER INFORMATION: A synthetic degenerate Forward Primer 1- Enone
      oxidoreductase

<400> SEQUENCE: 1
gtkgtkgctg cwkcyvttaa yc                                            22

<210> SEQ ID NO 2
<211> LENGTH: 22
<212> TYPE: DNA
<213> ORGANISM: ARTIFICIAL SEQUENCE
<220> FEATURE:
<223> OTHER INFORMATION: A synthetic degenerate Forward Primer 2- Enone
      oxidoreductase

<400> SEQUENCE: 2
aargmyayyg aytctccyyt rc                                            22

<210> SEQ ID NO 3
<211> LENGTH: 23
<212> TYPE: DNA
<213> ORGANISM: ARTIFICIAL SEQUENCE
<220> FEATURE:
<223> OTHER INFORMATION: A synthetic degenerate Forward Primer 3- Enone
      oxidoreductase

<400> SEQUENCE: 3
ggvwswttrg cwgartayac hgc                                           23

<210> SEQ ID NO 4
<211> LENGTH: 26
<212> TYPE: DNA
<213> ORGANISM: ARTIFICIAL SEQUENCE
<220> FEATURE:
<223> OTHER INFORMATION: A synthetic degenerate Forward Primer 4- Enone
      oxidoreductase

<400> SEQUENCE: 4
gttytrrrwg ghgctggkgg wgttgg                                        26

<210> SEQ ID NO 5
<211> LENGTH: 25
<212> TYPE: DNA
<213> ORGANISM: ARTIFICIAL SEQUENCE
<220> FEATURE:
<223> OTHER INFORMATION: A synthetic degenerate Reverse Primer 1- Enone
      oxidoreductase

<400> SEQUENCE: 5
gratsggrta yayracyacy ttycc                                         25

<210> SEQ ID NO 6
<211> LENGTH: 23
<212> TYPE: DNA
<213> ORGANISM: ARTIFICIAL SEQUENCE
```

```
<220> FEATURE:
<223> OTHER INFORMATION: A synthetic degenerate Reverse Primer 2- Enone
      oxidoreductase

<400> SEQUENCE: 6
gcyythtchs kytsyccway tgc                                           23

<210> SEQ ID NO 7
<211> LENGTH: 24
<212> TYPE: DNA
<213> ORGANISM: ARTIFICIAL SEQUENCE
<220> FEATURE:
<223> OTHER INFORMATION: A synthetic degenerate Reverse Primer 3- Enone
      oxidoreductase

<400> SEQUENCE: 7
rgtrgctgct ayyttdgawg cacc                                          24

<210> SEQ ID NO 8
<211> LENGTH: 23
<212> TYPE: DNA
<213> ORGANISM: ARTIFICIAL SEQUENCE
<220> FEATURE:
<223> OTHER INFORMATION: A synthetic gene specific Forward Primer 1-
      Enone oxidoreductase

<400> SEQUENCE: 8
cgaagacagg gcaagttcaa ggc                                           23

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: A synthetic gene specific Forward Primer 2-
      Enone oxidoreductase

<400> SEQUENCE: 9
ggtgttggaa gcttggtgat tcag                                          24

<210> SEQ ID NO 10
<211> LENGTH: 23
<212> TYPE: DNA
<213> ORGANISM: ARTIFICIAL SEQUENCE
<220> FEATURE:
<223> OTHER INFORMATION: A synthetic gene specific Reverse Primer 1-
      Enone oxidoreductase

<400> SEQUENCE: 10
gattctcccc tcccgactgt tcc                                           23

<210> SEQ ID NO 11
<211> LENGTH: 26
<212> TYPE: DNA
<213> ORGANISM: ARTIFICIAL SEQUENCE
<220> FEATURE:
<223> OTHER INFORMATION: A synthetic gene specific Reverse Primer 1-
      Enone oxidoreductase

<400> SEQUENCE: 11
gggttctctg ctggtaaatc tattct                                        26

<210> SEQ ID NO 12
<211> LENGTH: 22
<212> TYPE: DNA
<213> ORGANISM: ARTIFICIAL SEQUENCE
<220> FEATURE:
```

```
<223> OTHER INFORMATION: A synthetic terminal Primer Forward- Enone
      oxidoreductase

<400> SEQUENCE: 12
atgaaagcgt gggtgtatgg ag                                              22

<210> SEQ ID NO 13
<211> LENGTH: 25
<212> TYPE: DNA
<213> ORGANISM: ARTIFICIAL SEQUENCE
<220> FEATURE:
<223> OTHER INFORMATION: A synthetic terminal Primer Reverse- Enone
      oxidoreductase

<400> SEQUENCE: 13
ttaaggaatt gggtatataa ccacc                                           25

<210> SEQ ID NO 14
<211> LENGTH: 1204
<212> TYPE: DNA
<213> ORGANISM: Mangifera indica

<400> SEQUENCE: 14
atggaaacca tactagcatc agcaccttct aaattcacaa gcttccactc attttctcag     60
aggttctccc tcgccttccg ggaaaataga aggaaaaacg ttgtcaacgt taacggagcg    120
tcatcgtctt accttcctct aatagttaga gcaaattcac aagctgctcc tgcatccact    180
gaggccacca aggtgagtag tgtacccagt gaaatgaaag cgtgggtgta tggagaatat    240
ggaggagtcg atgtattgaa atttgatgag aaagtttctg tgcctcaagt gaaggaagat    300
caggtgttga tcaaggttgt tgctgcggct cttaatcctg ttgatgctaa gcgaagacag    360
ggcaagttca aggccaccga ttctcccctc ccgactgttc cagggtatga tgtagctggt    420
gtggtggtca aggttggcag tcaagtgaag gaatttaagg agggagatga ggtatatggg    480
gacataaatg agaaggcact ggaagggccg aaacaatttg ctccttagc cgagtacacc     540 gcagttgaag aaaagttatt ggcactgaaa ccaaaaaatt tggattttgt tcaggctgct    600
ggccttcctc ttgctattga acggcctat gagggtctag aaagaactgg ttctctgct      660 ggtaaatcta ttcttgtttt gaatggttct ggtggtgttg aagcttggt gattcagcta     720 gcaaacaag tatttggtgc ttcaaaagtt gccgcaactt caggaaccag aaacttggaa     780
cttttgaaga gcttgggtac tgatttggct attgactaca ccaaagaaaa tattgaagat    840
ttgccagaaa agtttgatgt ggtctatgat gctattgggc aatgtgatcg agcagtaaag    900
gtagtgaaag aaggggggtgc tgtggtggcc ctaacaggtg ctgtaacacc tccaggcttc    960
agatttgtag ttacttcaaa tggagctgtt ctgaaaaaat taaatgcatt tctagagagt    1020
ggaaaggtaa agcctgtaat agaccccaag gggccatttc ctttcagcca ggttattgag    1080
gctttctctt acattgaaac gaacagagct actggaaagg tggttatata cccaattcct    1140
taaaatcact agtgaattcg cggccgcctg caggtcgacc atatgggaga gctcccaacg    1200
cgtt                                                                 1204

<210> SEQ ID NO 15
<211> LENGTH: 1143
<212> TYPE: DNA
<213> ORGANISM: Mangifera indica

<400> SEQUENCE: 15
atggaaacca tactagcatc agcaccttct aaattcacaa gcttccactc attttctcag     60
```

-continued

```
aggttctccc tcgccttccg ggaaaataga aggaaaaacg ttgtcaacgt taacggagcg      120
tcatcgtctt accttcctct aatagttaga gcaaattcac aagctgctcc tgcatccact      180
gaggccacca aggtgagtag tgtacccagt gaaatgaaag cgtgggtgta tggagaatat      240
ggaggagtcg atgtattgaa atttgatgag aaagtttctg tgcctcaagt gaaggaagat      300
caggtgttga tcaaggttgt tgctgcggct cttaatcctg ttgatgctaa gcgaagacag      360
ggcaagttca aggccaccga ttctccctc ccgactgttc agggtatga tgtagctggt       420 gtggtggtca aggttggcag tcaagtgaag gaatttaagg agggagatga ggtatatggg      480
gacataaatg agaaggcact ggaagggccg aaacaatttg gctccttagc cgagtacacc      540
gcagttgaag aaaagttatt ggcactgaaa ccaaaaaatt tggattttgt tcaggctgct      600
ggccttcctc ttgctattga gacggcctat gagggtctag aaagaactgg gttctctgct      660
ggtaaatcta ttcttgtttt gaatggttct ggtggtgttg aagcttggt gattcagcta       720 gcaaaacaag tatttggtgc ttcaaaagtt gccgcaactt caggaaccag aaacttggaa      780
cttttgaaga gcttgggtac tgatttggct attgactaca ccaaagaaaa tattgaagat      840
ttgccagaaa agtttgatgt ggtctatgat gctattgggc aatgtgatcg agcagtaaag      900
gtagtgaaag aagggggtgc tgtggtggcc ctaacaggtg ctgtaacacc tccaggcttc      960
agatttgtag ttacttcaaa tggagctgtt ctgaaaaaat taaatgcatt tctagagagt     1020
ggaaaggtaa agcctgtaat agaccccaag gggccatttc ctttcagcca ggttattgag     1080
gctttctctt acattgaaac gaacagagct actggaaagg tggttatata cccaattcct     1140
taa                                                                    1143
```

<210> SEQ ID NO 16
<211> LENGTH: 23
<212> TYPE: DNA
<213> ORGANISM: ARTIFICIAL SEQUENCE
<220> FEATURE:
<223> OTHER INFORMATION: A synthetic Primer

<400> SEQUENCE: 16
aggtgctgta acacctccag gct                                               23

<210> SEQ ID NO 17
<211> LENGTH: 23
<212> TYPE: DNA
<213> ORGANISM: ARTIFICIAL SEQUENCE
<220> FEATURE:
<223> OTHER INFORMATION: A synthetic Primer

<400> SEQUENCE: 17
cctggctgaa aggaaatggc ccc                                               23

<210> SEQ ID NO 18
<211> LENGTH: 321
<212> TYPE: PRT
<213> ORGANISM: Fragaria ananassa

<400> SEQUENCE: 18

Met Ala Ala Ala Pro Ser Glu Ser Ile Pro Ser Val Asn Lys Ala Trp
 1               5                  10                  15

Val Tyr Ser Glu Tyr Gly Lys Thr Ser Asp Val Leu Lys Phe Asp Pro
             20                  25                  30

Ser Val Ala Val Pro Glu Val Lys Glu Asp Gln Val Leu Ile Lys Val
         35                  40                  45

```
Val Ala Ala Ser Leu Asn Pro Val Phe Lys Arg Ala Leu Gly Tyr Phe
        50                  55                  60

Lys Asp Thr Asp Ser Pro Leu Pro Thr Val Pro Gly Tyr Asp Val Ala
 65                  70                  75                  80

Gly Val Val Lys Val Gly Ser Gln Val Thr Lys Phe Lys Val Gly
                 85                  90                  95

Asp Glu Val Tyr Gly Asp Leu Asn Glu Ala Ala Leu Val Asn Pro Thr
                100                 105                 110

Arg Phe Gly Ser Leu Ala Glu Tyr Thr Ala Ala Asp Glu Arg Val Leu
                115                 120                 125

Ala His Lys Pro Lys Asp Leu Ser Phe Ile Glu Ala Ala Ser Leu Pro
                130                 135                 140

Leu Ala Ile Glu Thr Ala Tyr Glu Gly Leu Glu Arg Ala Glu Leu Ser
145                 150                 155                 160

Ala Gly Lys Ser Ile Leu Val Leu Gly Ala Gly Gly Val Gly Thr
                165                 170                 175

His Ile Ile Gln Leu Ala Lys His Val Phe Gly Ala Ser Lys Val Ala
                180                 185                 190

Ala Thr Ala Ser Thr Lys Lys Leu Asp Phe Leu Arg Thr Leu Gly Val
                195                 200                 205

Asp Leu Ala Ile Asp Tyr Thr Lys Glu Asn Ile Glu Asp Leu Pro Glu
                210                 215                 220

Lys Phe Asp Val Val Tyr Asp Ala Val Gly Glu Thr Asp Lys Ala Val
225                 230                 235                 240

Lys Ala Val Lys Glu Gly Gly Lys Val Val Thr Ile Val Gly Pro Ala
                245                 250                 255

Thr Pro Pro Ala Ile His Phe Val Leu Thr Ser Lys Gly Ser Val Leu
                260                 265                 270

Glu Lys Leu Lys Pro Tyr Leu Glu Ser Gly Lys Val Lys Pro Val Leu
                275                 280                 285

Asp Pro Thr Ser Pro Tyr Pro Phe Thr Lys Leu Val Glu Ala Phe Gly
                290                 295                 300

Tyr Leu Glu Ser Ser Arg Ala Thr Gly Lys Val Val Val Tyr Pro Ile
305                 310                 315                 320

Pro

<210> SEQ ID NO 19
<211> LENGTH: 388
<212> TYPE: PRT
<213> ORGANISM: Solanum lycopersicum

<400> SEQUENCE: 19

Met Glu Ala Leu Leu Ser Ser Thr Thr Leu Gln Leu Lys Pro Leu His
  1               5                  10                  15

Pro Pro Ser Ser Phe Ser Ser Leu His Ser Pro Phe Ser Ser Ile Ser
                 20                  25                  30

Val Leu Arg Val Lys Gly Ser Lys Lys Ala Glu Thr Phe Ile Gln Arg
                 35                  40                  45

Ser Asn Phe Ser Thr Val Leu Pro Leu Arg Val Ser Ala Ser Ser Gln
 50                  55                  60

Ala Ala Ala Ala Glu Thr Ser Thr Ser Ile Ser Ile Pro Ser Glu Met
 65                  70                  75                  80

Lys Ala Trp Ser Tyr Thr Asp Tyr Gly Ser Val Asp Val Leu Lys Leu
                 85                  90                  95
```

Glu Ser Asn Val Ala Val Pro Asp Ile Lys Glu Asp Gln Val Leu Ile
                100                 105                 110

Lys Ile Val Ala Ala Ala Leu Asn Pro Val Asp Phe Lys Arg Arg Leu
            115                 120                 125

Gly Lys Phe Lys Ala Thr Asp Ser Pro Ala Ala Leu Pro Leu Ala Ile
130                 135                 140

Glu Thr Ala Tyr Glu Gly Leu Glu Lys Ala Gly Phe Ser Ser Gly Lys
145                 150                 155                 160

Ser Ile Leu Val Leu Gly Ala Gly Val Gly Ser Leu Val Ile
                165                 170                 175

Gln Leu Ala Lys His Val Phe Gly Ala Ser Lys Val Ala Thr Ser
            180                 185                 190

Ser Thr Gly Lys Leu Glu Leu Leu Lys Ser Leu Gly Ala Asp Leu Ala
            195                 200                 205

Ala Leu Pro Leu Ala Ile Glu Thr Ala Tyr Glu Gly Leu Glu Lys Ala
210                 215                 220

Gly Phe Ser Ser Gly Lys Ser Ile Leu Val Leu Gly Ala Gly Gly
225                 230                 235                 240

Val Gly Ser Leu Val Ile Gln Leu Ala Lys His Val Phe Gly Ala Ser
            245                 250                 255

Lys Val Ala Ala Thr Ser Ser Thr Gly Lys Leu Glu Leu Leu Lys Ser
            260                 265                 270

Leu Gly Ala Asp Leu Ala Ile Asp Tyr Thr Lys Glu Asn Phe Glu Asp
            275                 280                 285

Leu Pro Asp Lys Phe Asp Val Val Tyr Asp Ser Val Gly Gln Gly Glu
            290                 295                 300

Lys Ala Val Lys Val Lys Glu Gly Gly Ser Val Val Val Leu Thr
305                 310                 315                 320

Gly Ala Val Thr Pro Pro Gly Phe Arg Phe Val Val Thr Ser Asn Gly
                325                 330                 335

Glu Met Leu Lys Lys Leu Asn Pro Tyr Leu Glu Ser Gly Lys Val Lys
            340                 345                 350

Pro Val Ile Asp Pro Lys Gly Pro Phe Ser Phe Asp Lys Val Val Asp
            355                 360                 365

Ala Phe Ser Tyr Leu Glu Thr Gly Arg Ala Thr Gly Lys Val Val Ile
370                 375                 380

His Pro Ile Pro
385

<210> SEQ ID NO 20
<211> LENGTH: 379
<212> TYPE: PRT
<213> ORGANISM: Mangifera indica

<400> SEQUENCE: 20

Met Glu Thr Ile Leu Ala Ser Ala Pro Ser Lys Phe Thr Ser Phe His
  1               5                  10                  15

Ser Phe Ser Gln Arg Phe Ser Leu Ala Phe Arg Glu Asn Arg Arg Lys
                20                  25                  30

Asn Val Val Asn Val Asn Gly Ala Ser Ser Tyr Leu Pro Leu Ile
            35                  40                  45

Val Arg Ala Asn Ser Gln Ala Ala Pro Ala Ser Thr Glu Ala Thr Lys
50                  55                  60

Val Ser Ser Val Pro Ser Glu Met Lys Ala Trp Val Tyr Gly Glu Tyr

```
                65                  70                  75                  80
        Gly Gly Val Asp Val Leu Lys Phe Asp Glu Lys Val Ser Val Pro Gln
                        85                  90                  95

Val Lys Glu Asp Gln Val Leu Ile Lys Val Ala Ala Ala Leu Asn
                        100                 105                 110

Pro Val Asp Ala Lys Arg Arg Cys Gly Lys Phe Lys Ala Thr Asp Ser
                        115                 120                 125

Pro Leu Pro Thr Val Pro Gly Tyr Asp Val Ala Gly Val Val Lys
                        130                 135                 140

Val Gly Ser Gln Val Lys Glu Phe Lys Glu Gly Asp Glu Val Tyr Gly
        145                 150                 155                 160

Asp Ile Asn Glu Lys Ala Leu Glu Gly Pro Lys Gln Phe Gly Ser Leu
                        165                 170                 175

Ala Glu Tyr Thr Ala Val Glu Glu Lys Leu Leu Ala Leu Lys Pro Lys
                        180                 185                 190

Asn Leu Asp Phe Val Gln Ala Ala Gly Leu Pro Leu Ala Ile Glu Thr
                        195                 200                 205

Ala Tyr Glu Gly Leu Glu Arg Thr Gly Phe Ser Ala Gly Lys Ser Ile
                        210                 215                 220

Leu Val Leu Asn Gly Ser Gly Gly Val Gly Ser Leu Val Ile Gln Leu
        225                 230                 235                 240

Ala Lys Gln Val Phe Gly Ala Ser Lys Val Ala Thr Ser Gly Thr
                        245                 250                 255

Arg Asn Leu Glu Leu Leu Lys Ser Leu Gly Thr Asp Leu Ala Ile Asp
                        260                 265                 270

Tyr Thr Lys Glu Asn Ile Glu Asp Leu Pro Glu Lys Phe Asp Val Val
                        275                 280                 285

Tyr Asp Ala Ile Gly Gln Cys Asp Arg Ala Val Lys Val Val Lys Glu
                        290                 295                 300

Gly Gly Ala Val Val Ala Leu Thr Gly Ala Val Thr Pro Pro Gly Phe
        305                 310                 315                 320

Arg Phe Val Val Thr Ser Asn Gly Val Leu Lys Lys Leu Asn Ala Phe
                        325                 330                 335

Leu Glu Ser Gly Lys Val Lys Pro Val Ile Asp Pro Lys Gly Pro Phe
                        340                 345                 350

Pro Phe Ser Gln Val Ile Glu Ala Phe Ser Tyr Ile Glu Thr Asn Arg
                        355                 360                 365

Ala Thr Gly Lys Val Val Ile Tyr Pro Ile Pro
                        370                 375

<210> SEQ ID NO 21
<211> LENGTH: 383
<212> TYPE: PRT
<213> ORGANISM: Cucumis sativus

<400> SEQUENCE: 21

Met Ala Ala Ile Leu Ala Ser Thr Pro Ser Gln Leu Asn Ser Tyr Cys
1               5                   10                  15

His Phe Ile Ser Ser Lys Leu Cys Pro Ser Phe Ser Leu Ser Leu Arg
                20                  25                  30

Gln Ser Asn Arg Lys Thr Ile Gly Tyr Ser Pro Val Ser Ser Arg Ile
                35                  40                  45

Arg Leu Arg Val Phe Ala Asn Ser Gln Ser Ala Pro Ala Ser Val Val
                50                  55                  60
```

```
Thr Ser Glu Val Ala Ser Val Pro Ser Glu Met Lys Ala Trp Val Tyr
 65                  70                  75                  80

Gly Glu Tyr Gly Gly Val Asp Val Leu Lys Phe Asp Ser Ser Val Ser
                 85                  90                  95

Phe Pro Glu Val Lys Glu Asp Gln Val Leu Ile Lys Val Val Ala Ala
                100                 105                 110

Ala Leu Asn Pro Val Asp Gly Lys Arg Met Leu Gly Lys Phe Lys Ala
                115                 120                 125

Thr Asp Ser Pro Leu Pro Thr Val Pro Gly Tyr Asp Val Ala Gly Val
130                 135                 140

Val Val Lys Val Gly Ser Gln Val Lys Glu Leu Lys Glu Gly Asp Glu
145                 150                 155                 160

Val Tyr Gly Asn Ile Asn Glu Lys Ala Leu Asp Gly Pro Lys Gln Phe
                165                 170                 175

Gly Ser Leu Ala Glu Tyr Thr Ala Val Glu Glu Lys Leu Leu Ala Val
                180                 185                 190

Lys Pro Lys Asn Ile Asp Phe Val Gln Ala Ala Gly Leu Pro Leu Ala
                195                 200                 205

Ile Glu Thr Ala Tyr Glu Gly Leu Glu Lys Thr Asn Phe Ser Thr Gly
210                 215                 220

Lys Ser Ile Leu Val Leu Asn Gly Ala Gly Gly Val Gly Ser Leu Val
225                 230                 235                 240

Ile Gln Leu Ala Lys Asn Val Phe Gly Ala Ser Lys Val Ala Ala Thr
                245                 250                 255

Ala Ser Thr Gly Lys Leu Glu Phe Leu Lys Ser Leu Gly Val Asp Leu
                260                 265                 270

Ala Ile Asp Tyr Thr Lys Glu Asn Ile Glu Asp Leu Pro Glu Lys Phe
                275                 280                 285

Asp Val Val Tyr Asp Ala Ile Gly Gln Cys Asp Lys Ala Val Lys Val
                290                 295                 300

Val Lys Lys Gly Gly Ser Val Val Ala Leu Thr Gly Ala Val Thr Pro
305                 310                 315                 320

Pro Gly Phe Arg Phe Val Val Thr Ser Asp Gly Ala Val Leu Lys Lys
                325                 330                 335

Leu Asn Pro Tyr Leu Glu Ser Gly Lys Val Lys Pro Ile Val Asp Pro
                340                 345                 350

Lys Gly Pro Phe Ser Phe Ser Gln Val Val Glu Ala Phe Ala Tyr Val
                355                 360                 365

Glu Ser Ser Arg Ala Thr Gly Lys Val Val Ile His Pro Ile Pro
370                 375                 380

<210> SEQ ID NO 22
<211> LENGTH: 386
<212> TYPE: PRT
<213> ORGANISM: Arabidopsis thaliana

<400> SEQUENCE: 22

Met Asn Ala Ala Leu Ala Thr Thr Ala Thr Thr Pro Val Leu Arg
 1               5                  10                  15

Arg Glu Thr Pro Leu Leu His Tyr Cys Ser Leu Thr Thr Lys Ser Pro
                 20                  25                  30

Val Tyr Gln Ile Asn Arg Val Arg Phe Gly Ser Cys Val Gln Thr Val
                 35                  40                  45

Ser Lys Lys Phe Leu Lys Ile Ser Ala Ser Ser Gln Ser Ala Ser Ala
 50                  55                  60
```

```
Ala Val Asn Val Thr Ala Asp Ala Ser Ile Pro Lys Glu Met Lys Ala
 65              70                  75                  80

Trp Val Tyr Ser Asp Tyr Gly Gly Val Asp Val Leu Lys Leu Glu Ser
             85                  90                  95

Asn Ile Val Val Pro Glu Ile Lys Glu Asp Gln Val Leu Ile Lys Val
            100                 105                 110

Val Ala Ala Ala Leu Asn Pro Val Asp Ala Lys Arg Arg Gln Gly Lys
            115                 120                 125

Phe Lys Ala Thr Asp Ser Pro Leu Pro Thr Val Pro Gly Tyr Asp Val
            130                 135                 140

Ala Gly Val Val Val Lys Val Gly Ser Ala Val Lys Asp Leu Lys Glu
145                 150                 155                 160

Gly Asp Glu Val Tyr Ala Asn Val Ser Glu Lys Ala Leu Glu Gly Pro
                165                 170                 175

Lys Gln Phe Gly Ser Leu Ala Glu Tyr Thr Ala Val Glu Glu Lys Leu
            180                 185                 190

Leu Ala Leu Lys Pro Lys Asn Ile Asp Phe Ala Gln Ala Ala Gly Leu
            195                 200                 205

Pro Leu Ala Ile Glu Thr Ala Asp Glu Gly Leu Val Arg Thr Glu Phe
            210                 215                 220

Ser Ala Gly Lys Ser Ile Leu Val Leu Asn Gly Ala Gly Gly Val Gly
225                 230                 235                 240

Ser Leu Val Ile Gln Leu Ala Lys His Val Tyr Gly Ala Ser Lys Val
            245                 250                 255

Ala Ala Thr Ala Ser Thr Glu Lys Leu Glu Leu Val Arg Ser Leu Gly
            260                 265                 270

Ala Asp Leu Ala Ile Asp Tyr Thr Lys Glu Asn Ile Glu Asp Leu Pro
            275                 280                 285

Asp Lys Tyr Asp Val Val Phe Asp Ala Ile Gly Met Cys Asp Lys Ala
            290                 295                 300

Val Lys Val Ile Lys Glu Gly Gly Lys Val Val Ala Leu Thr Gly Ala
305                 310                 315                 320

Val Thr Pro Pro Gly Phe Arg Phe Val Val Thr Ser Asn Gly Asp Val
            325                 330                 335

Leu Lys Lys Leu Asn Pro Tyr Ile Glu Ser Gly Lys Val Lys Pro Val
            340                 345                 350

Val Asp Pro Lys Gly Pro Phe Pro Phe Ser Arg Val Ala Asp Ala Phe
            355                 360                 365

Ser Tyr Leu Glu Thr Asn His Ala Thr Gly Lys Val Val Val Tyr Pro
            370                 375                 380

Ile Pro
385
```